(12) United States Patent
Sinha (10) Patent No.: US 12,114,674 B2
(45) Date of Patent: Oct. 15, 2024

(54) DESTRUCTION OF AIRBORNE PATHOGENS, AND MICROORGANISMS ON GRAINS AND DRIED FOOD USING ULTRASOUND

(71) Applicant: AWE Technologies, LLC, Bay Shore, NY (US)

(72) Inventor: Dipen N. Sinha, Bay Shore, NY (US)

(73) Assignee: AWB Technologies, LLC, Bay Shore, NY (US)

( * ) Notice: Subject to any disclaimer, the term of this patent is extended or adjusted under 35 U.S.C. 154(b) by 83 days.

(21) Appl. No.: 17/349,525

(22) Filed: Jun. 16, 2021

(65) Prior Publication Data
US 2021/0392911 A1 Dec. 23, 2021

Related U.S. Application Data

(60) Provisional application No. 63/040,259, filed on Jun. 17, 2020.

(51) Int. Cl.
*A61L 2/00* (2006.01)
*A23B 9/00* (2006.01)
(Continued)

(52) U.S. Cl.
CPC ............... *A23B 9/005* (2013.01); *A23B 9/06* (2013.01); *A23L 3/001* (2013.01); *A23L 3/015* (2013.01);
(Continued)

(58) Field of Classification Search
CPC ........... A61L 2/025; A61L 9/16; A23B 9/005; A01G 22/00; A23L 33/105; B22D 11/115; B22D 11/003; B65B 37/14
(Continued)

(56) References Cited

U.S. PATENT DOCUMENTS 3,956,031 A * 5/1976 Marcus ..................... H01F 1/06
148/105
4,141,404 A * 2/1979 McMullen ................ B22C 5/08
134/57 R
(Continued)

FOREIGN PATENT DOCUMENTS

WO WO9103415 A1 3/1991
WO WO2018104955 A1 6/2018
WO WO2019089661 A1 5/2019

OTHER PUBLICATIONS

PCT/US21/37660 to AWE Technologies, LLC, International Search Report and Written Opinion, mailed Nov. 10, 2021.

*Primary Examiner* — Monzer R Chorbaji
(74) *Attorney, Agent, or Firm* — Samuel M. Freund; Cochran Freund & Young LLC (57) ABSTRACT

An acoustic apparatus and method for using a combination of low-frequency and high-frequency vibration of dried food, grain being an example, such that there are a large number of collisions among the individual grain particles for destroying microorganisms that reside on the surface or just below the surface of the grain, are described. Embodiments of the invention permit bulk and continuous processing of the food. It is expected that such collisions do not produce any chemical changes in the food, nor should it have any adverse effects on the taste thereof. Embodiments of the apparatus are applicable to destruction of airborne microorganisms.

12 Claims, 4 Drawing Sheets

(51) Int. Cl.
- *A23B 9/06* (2006.01)
- *A23L 3/00* (2006.01)
- *A23L 3/015* (2006.01)
- *A23L 3/32* (2006.01)
- *A61L 9/16* (2006.01)
- *B06B 1/00* (2006.01)
- *B65G 15/32* (2006.01)

(52) U.S. Cl.
CPC ................................ *A23L 3/32* (2013.01); *A61L 9/16* (2013.01); *B65G 15/32* (2013.01); *A61L 2209/14* (2013.01); *B65G 2201/0202* (2013.01)

(58) Field of Classification Search
USPC ............ 422/20, 127–128, 286, 300; 426/320
See application file for complete search history.

(56) References Cited

U.S. PATENT DOCUMENTS

| | | | |
|---|---|---|---|
| 5,496,411 | A | 3/1996 | Candy |
| 6,269,618 | B1 * | 8/2001 | Digman ................ A01F 12/16 460/106 |
| 2004/0022907 | A1 | 2/2004 | Mielnik et al. |
| 2004/0028552 | A1 | 2/2004 | Bhardwaj et al. |
| 2005/0167247 | A1 | 8/2005 | Chojnacki |
| 2006/0015045 | A1 | 1/2006 | Zets et al. |
| 2011/0048251 | A1 | 3/2011 | Bardenshtein et al. |

* cited by examiner

DESTRUCTION OF AIRBORNE PATHOGENS, AND MICROORGANISMS ON GRAINS AND DRIED FOOD USING ULTRASOUND

CROSS-REFERENCE TO RELATED APPLICATIONS

The present application claims the benefit of U.S. Provisional Patent Application No. 63/040,259 for "Destruction Of Airborne Pathogens, And Microorganisms On Grains And Dried Food Using Ultrasound", which was filed on 17 Jun. 2020, the entire content of which Patent Application is hereby specifically incorporated by reference herein for all that it discloses and teaches.

BACKGROUND

Microorganisms, especially heat-resistant bacterial spores, although they are widely used for food processing, frequently contaminate grains, pulses (peas, beans and lentils), spices and dehydrated vegetables causing spoilage. Bacterial spores contaminating these dry food ingredients cannot be completely inactivated by heating processes, such as steaming and boiling at food processing plants. Thus, dry ingredients for food processing need to be decontaminated to prevent food spoilage and food-borne diseases. Decontamination techniques including fumigation with ethylene oxide gas (EOG), irradiation with ionizing radiation, and treatment with super-heated steam have been applied to some of the dry food ingredients.

However, these techniques are not without drawbacks. EOG fumigation is prohibited in certain countries because of the carcinogenic effect of the residues. Irradiation with gamma rays or electron beams can effectively inactivate bacterial spores contaminating spices and dehydrated vegetables with minimal quality alteration, and irradiation of spices is practiced on a commercial basis in more than 20 countries. However, irradiation of food products other than potatoes is not approved in several countries. Irradiation at high doses for decontamination is not applicable to grains such as rice and wheat, since ionizing radiation causes oxidation and degradation of components such as lipid and starch molecules, which results in flavor and texture quality deterioration of grain products such as noodles and rice cakes. Irradiation also causes chemical changes in food, producing substances not known to be present in non-irradiated food. These substances, are called "radio-lytic products". However, any treatment causes chemical changes in food. For example, heat treatment, or cooking, produces chemicals that are known as "thermolytic products", which have been found to mirror those created by cooking.

Treatment with super-heated steam is the only method widely used for decontaminating dry ingredients in Japan. However, super-heated steam sometimes brings about changes of flavor and color of dehydrated vegetables and herbs.

With the recent pandemic involving COVID-19, there is even a greater emphasis on removing airborne pathogens than prior to the arrival of this deadly virus. As is now well-substantiated, human-to-human infection through expiration of droplet laden virus is the most common mode of transfer.

SUMMARY

In accordance with the purposes of the present invention, as embodied and broadly described herein, an embodiment of the method for destruction of microorganisms residing on the surfaces of grains or dried food disposed in a container having a surface, hereof, includes: applying a first periodic vibrational excitation having a first amplitude to the surface of the container effective for causing the grains or dried food disposed therein to be become airborne; and applying a second periodic vibrational excitation having a second amplitude to the surface of the container effective for causing the airborne grains or dried food to undergo increased collisions therebetween; whereby the microorganisms are destroyed by collisions of the airborne grain or the dried food.

In another aspect of the present invention, and in accordance with its purposes, an embodiment of the method for destruction of microorganisms residing on the surfaces of grains and dried food, hereof, includes: depositing grains or dried food on the surface of a moving conveyor belt; applying a first periodic vibrational excitation having a first amplitude to the conveyor belt effective for creating a fluidized bed of the grains or dried food above the surface of the conveyor belt; and applying a second periodic vibrational excitation having a second amplitude to the fluidized grains or dried food effective for causing the grains or dried food to undergo increased collisions therebetween; whereby the microorganisms are destroyed by collisions of the grain or dried food.

In yet another aspect of the present invention, and in accordance with its purposes, an embodiment of the method for destruction of pathogens attached to airborne particles, hereof, includes: causing the air to flow in a selected direction; generating a first periodic acoustic wave in a first volume of the air flow having a first wavelength; reflecting the first periodic acoustic wave in the first volume of the air flow, such that a first standing wave pattern of parallel nodal planes having a first chosen separation is produced, whereby clusters of the airborne particles having pathogens attached thereto are generated, the clusters moving in the flowing air; and generating a second periodic acoustic wave in a second volume of the air flow having a second wavelength; reflecting the second periodic acoustic wave, such that a second standing wave pattern of parallel nodal planes having a second chosen separation larger than the first chosen separation is produced downstream from the first volume of the air flow, whereby large numbers of collisions between the clusters of the airborne particles having pathogens attached thereto are generated; such that the pathogens are destroyed by collisions of the clusters.

In still another aspect of the present invention, and in accordance with its purposes, an embodiment of the apparatus for destruction of microorganisms residing on the surfaces of grains and dried food, hereof, includes: a conveyor belt having a trough-shaped carrying side onto which are deposited grains or dried food, and a lower side supported by at least one set of 3-roller trough idlers, each idler having an axle, and at least one head pulley and at least one tail pulley, said at least one head pulley being powered such that the conveyor belt is moved; a first source of vibration for applying a first periodic vibrational excitation having a first amplitude to the at least one set 3-roller trough idlers, effective for creating a fluidized bed of the grains or dried food above the surface of the conveyor belt; and a second source of periodic vibrational excitation having a second amplitude for vibrating the fluidized grains or dried food, effective for causing the grains or dried food to undergo increased collisions therebetween; whereby the microorganisms are destroyed by collisions of the grain or dried food.

Benefits and advantages of the present invention include, but are not limited to, providing an apparatus and method for destruction of microorganisms, such as viruses attached to larger particles, by causing numerous collisions among the larger particles using sound, and taking advantage of the mechanically fragile outer membranes of the microorganisms.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 3A is schematic representation of a cross-section of an embodiment of a conveyor system for continuous processing of grains for destruction of surface microorganisms, where rollers are disposed underneath the belt in such a manner that the belt maintains an open concave shape while riding on multiple sets of rollers suitable for containing grains as the grain is carried by the belt from one location to another, while

DETAILED DESCRIPTION

A. Bulk Destruction of Microorganisms in Dry Food Grains:

It is generally recognized that since most of the microorganisms contaminating dry food ingredients reside on the food surfaces, the inner portions do not have to be exposed to heat, gas or radiation for decontamination. Use of a vibrating surface to vibrate multiple layers of grain to be decontaminated in such a manner that it forms a fluidized bed where the grains are effectively floating on air, while continuously colliding with each other (A fluidized bed is a physical phenomenon occurring when a quantity of a solid particulate substance is placed under appropriate conditions to cause a solid/fluid mixture to behave as a fluid.). Such collisions do not generate chemical changes in the food and, therefore, should not have an adverse effect on its taste. It was observed that a single source of vibration from above was not very effective in creating such a collision condition. The effectiveness of collisions was determined by using dyed grains mixed with grains that were clean. The degree of spread of coloring in grain was a rapid visualization of the effectiveness of the collision process and the extent of the process. At high frequencies (between 60 kHz and 80 kHz), the grain material on top shielded the grain below. This happened when the grain was insonified from below as well. In the frequency range between 6 kHz and 15 kHz, the grain bed could be fluidized (lifted in air) only when insonified from below but showed no circulation. At the lowest frequency range, between about 20 Hz and about 80 Hz, there was fixed pattern circulation in the grain, but with isolated ranges with little or no motion of the grain. The sterilization effect was expected to be a function of number of collisions; therefore, the low frequencies were deemed unacceptably slow for practical applications. To address these concerns, a dual swept-frequency system was used.

A system found to be effective employed a low-frequency shaker/circulation platform, and a higher frequency grain collision section. Any source of vibration can be used, and it is not limited to the low-frequency audio speaker employed for circulating the grain in the grain sample. A square-wave electrical excitation of the audio speaker was found to be effective as it produced higher harmonics that assisted in eliminating regions where no excitation occurred. Additionally, for avoiding fixed patterns in the grain vibration or circulation, the square-wave frequency was varied between about 20 Hz and about 100 Hz in a linear manner at various rates, with a typical period being 2 s, and a 20%-50% duty cycle (with 50% being used in the EXAMPLES below). This frequency range was effective for the grain used, and may be varied for other grains. A mid-frequency (between about 6 kHz and 10 kHz) piezoelectric transducer was attached to and located directly below a lightweight plastic grain container. The temperature of the grain was measured using an inserted thermocouple.

For noninvasive batch processing, grain can be kept inside a chamber so that the material remains inside a chosen volume for the duration of the treatment. As stated, vibration frequencies can be of the order of 10 kHz. Frequency modulation or other means may be employed so that no standing wave patterns are generated in the grains, since grains in nodal areas do not undergo many collisions. However, any periodic waveform, variable or fixed frequency, can be employed with varying efficiency. Additionally, grains should remain airborne during the microorganism destruction process, so that grain collisions do not diminish. The temperature of the system does not need be controlled because any heat generated due to the vibration and collisions assists the process of microorganism destruction. The temperature inside the chamber was measured using thermocouples, and was found not to increase more than 4° C. during grain processing. However, the temperature increase depends on the duration of the excitation.

If a grain undergoes a few million collisions, the likelihood of breaking open a microorganism on the surface of the grain, due to the physical impact of one grain on another is significant. Further, for grains having sharp edges, the process of destruction should be facilitated.

Figure 1:
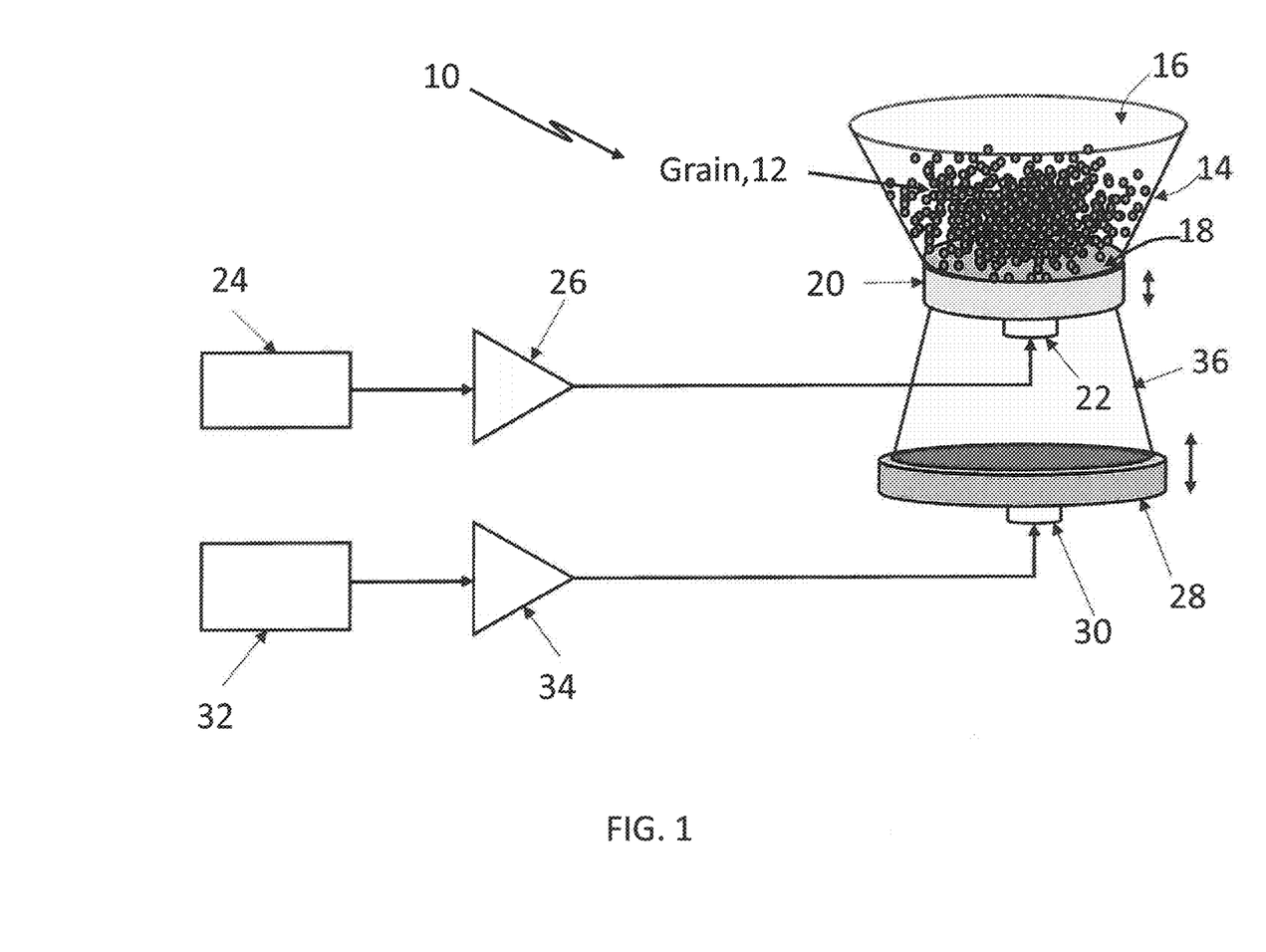
FIG. 1 is a schematic representation of a side perspective view of an embodiment of an apparatus for bulk processing of grains for destruction of surface microorganisms using two ultrasonic frequencies effective for inducing vibrations in a container holding the grains.
Figure 2:
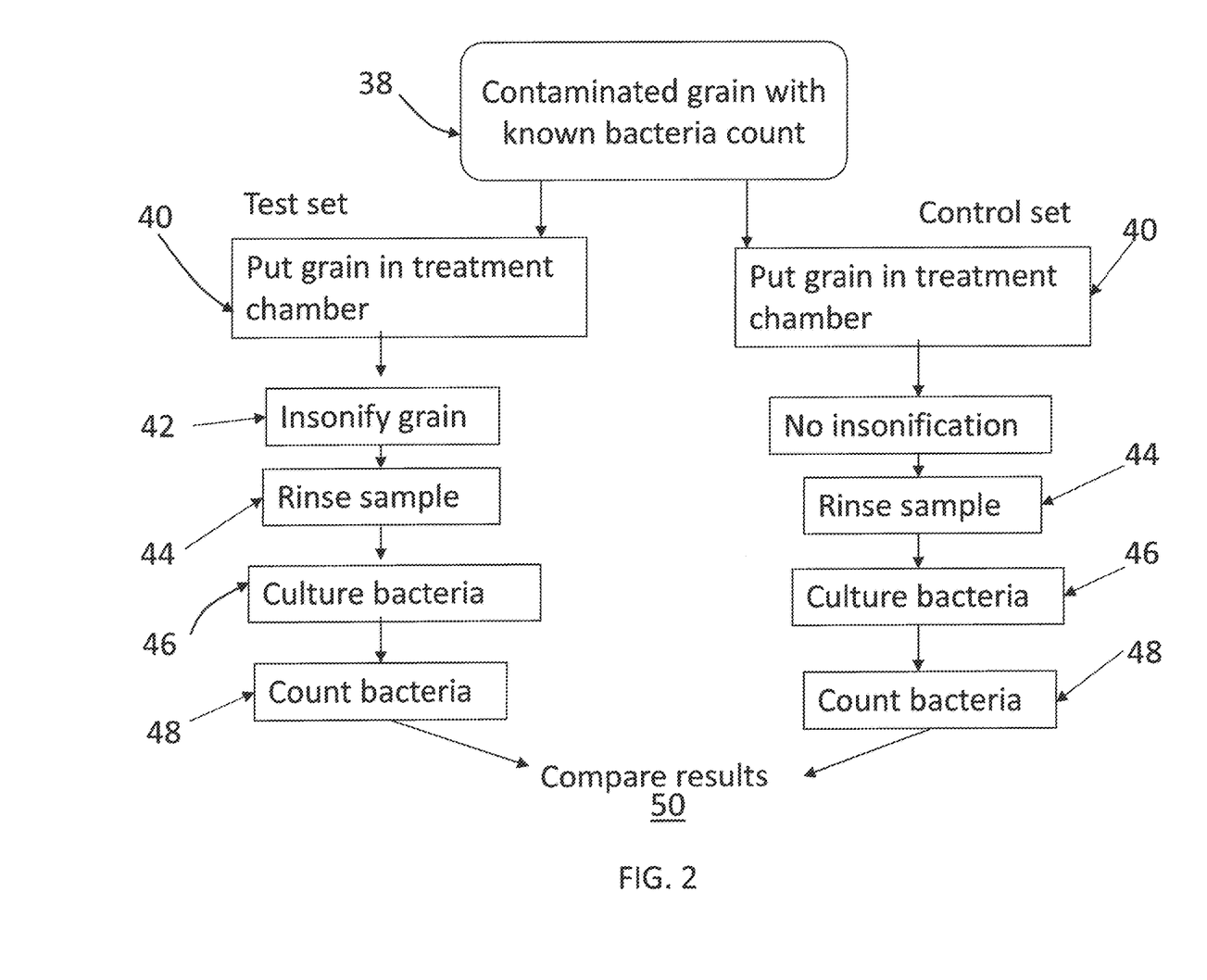
FIG. 2 describes an embodiment of the use of the apparatus in FIG. 1 in a proof of principle; after insonification of an infected sample at a chosen frequency for a selected time period, the grain is rinsed, the bacteria cultured and counted, and the results compared with another grain sample that has not been insonified, as a control set.

Reference will now be made in detail to the present embodiments of the invention, examples of which are illustrated in the accompanying drawings. In the Figures, similar structure will be identified using identical reference characters. It will be understood that the FIGURES are presented for the purpose of describing particular embodiments of the invention and are not intended to limit the invention thereto. Turning now to FIG. 1, illustrated is a schematic representation of a cross-section of an embodiment of apparatus, 10, for noninvasive bulk processing of grains, 12, for destruction of surface microorganisms. Grains were disposed in lightweight plastic container or chamber, 14, having lid, 16, and bottom, 18, resting on vibrating surface, 20. Vibrating surface 20, may itself be a transducer, or be driven by transducer, 22, in response to chosen signals from periodic waveform generator, 24, amplified to a selected voltage by amplifier 26, is used for shaking grains 12, once airborne. Transducer 22 was a mid-frequency (between about 6 kHz and 10 kHz) piezoelectric disk transducer, rated at 100 W. The temperature of the grain was measured using an inserted thermocouple. Frequencies in the tens of kHz, for example, 10 kHz, have been found to cause numerous collisions between the grains. For grains having smaller volumes and masses, higher frequencies (up to 100 kHz) are more effective.

Vibrating surface 28, which may itself be a transducer, or be driven by transducer, 30, in response to chosen signals from periodic waveform generator, 32, amplified to a selected voltage by amplifier 34, is used for circulating or agitating grains 12, such that they effectively become airborne. Surface 20 rests on rigid structure, 36, which may comprise a cylindrical or conical shape, as examples, constructed of plastic or metal, that rests on surface 28. As stated, frequencies in the tens of Hz have been found to generate a fluidized bed condition in grains 12 in container 14, whereby the grains are repeatedly ejected from bottom 18 of container 14, effectively becoming airborne, while at the same time continuously colliding with each other under the influence of the combination of vibrations from transducers 22 and 30. Signals from periodic waveform generator 32 may be swept in frequency. In the present apparatus, vibrating surface 28 comprised a mid-range audio speaker (tweeter) rated at 30 W producing a displacement of between about 2 mm and 5 mm, was to circulate the grain in the grain sample, although the present invention is not limited to the audio speaker used. Square-wave electrical excitation was found to be effective in eliminating fixed, standing-wave vibrational or circulation patterns in the grains where no excitation occurred, since it produced higher harmonics. Additionally, for avoiding fixed patterns in the grain vibration or circulation, the square-wave frequency was varied between about 20 Hz and about 100 Hz in a linear manner at various rates, with a typical period being 2 s and a duty cycle of 50%.

Amplifiers 26 and 34 (Pro PT-2000 units from Pyle), have a bandwidth of 80 kHz and are rated for up to 350 watts. An Agilent 34970A Data Acquisition Switch Unit, having a 34901A, 20 channel multiplexer, and type T thermocouples (not shown in FIG. 1) were used for temperature measurements.

FIG. 2 describes an embodiment of the use of the apparatus in FIG. 1 in a proof of principle. In step, 38, the grain is contaminated with a known quantity of microorganisms, in this case, bacteria, before placement, 40, in treatment container or chamber 14. After insonification, 42, at a chosen frequency for a selected time period, the grain is rinsed, 44, the bacteria cultured, 46, counted, 48, after being cultured, for a chosen period, and the results compared, 50, with another grain sample that has not been insonified, the control set. The following EXAMPLES illustrate an embodiment of the bulk method of the present invention.

Example 1

An approximately ¼-in-thick layer was formed by 4 g of wheat grain on the bottom 18 of container 12. Between 5 and 10 layers thick are expected to work effectively. The grain was then artificially contaminated with *Salmonella choleraesuis* (14028, Source: BD Diagnostic Systems Product name: BD BBL™ QualiSwab™ Quality Control Organism in accordance with the ITOCHU Procedure for Contamination of Grain. An identical sample was contaminated as a reference sample for comparison. The vibration frequencies, amplitudes, the FM modulation etc., used were not optimized, but multiple impacts of grain on grain clearly occurred. One sample was then subjected to the vibration decontamination method described in FIG. 2 for 10 min. The control sample was not insonified. Following the insonification, both samples were rinsed with distilled water and cultured. Each test was repeated three times, and the reported numbers are in units of CFU (Colony Forming Units). The first column shows the counts from the control sample, and the second column shows the results of bulk grain insonification.

The applied low-frequency vibration was a linearly swept square-wave between 28 Hz and 72 Hz over 2 s, having a displacement of between 2 mm and 5 mm, while the higher frequency vibration was a 15 V peak-to-peak linearly swept square-wave between 6 kHz and 9 kHz over 2 s, giving the following results:

| | Control (CFU) | Insonicated Grains (CFU) |
|---|---|---|
| | 714 | 536 |
| | 665 | 294 |
| | 944 | 372 |
| Average: | 774 | 401 |
| Average Reduction: | 48% | |

Example 2

A second culture of *Salmonella* bacteria was prepared and a second batch of grains was separately infected.

The applied low-frequency vibration was a linearly swept square-wave between 37 Hz and 58 Hz over 2 s, having a displacement of between 2 mm and 5 mm, while the higher frequency vibration was a 15 V peak-to-peak linearly swept square-wave between 6 kHz and 9 kHz over 2 s, giving the following results:

| | Control (CFU) | Insonicated Grains (CFU) |
|---|---|---|
| | 778 | 185 |
| | 628 | 121 |
| | 776 | 213 |
| Average: | 727 | 173 |
| Average Reduction: | 76% | |

B. Continuous Destruction of Microorganisms in Dry Food Grains:

As discussed above, bulk pathogen destruction in grains is a combination of two processes: (1) creating a fluidized bed of grains above a surface by vibrating the surface at a low frequency, and (2) then vibrating the grains at a much higher frequency so individual grains can collide with neighboring grains. For continuous processing of significantly larger quantities of grain, a similar approach may be applied to grains being transported on a trough-shaped conveyor belt.

Figure 3A:
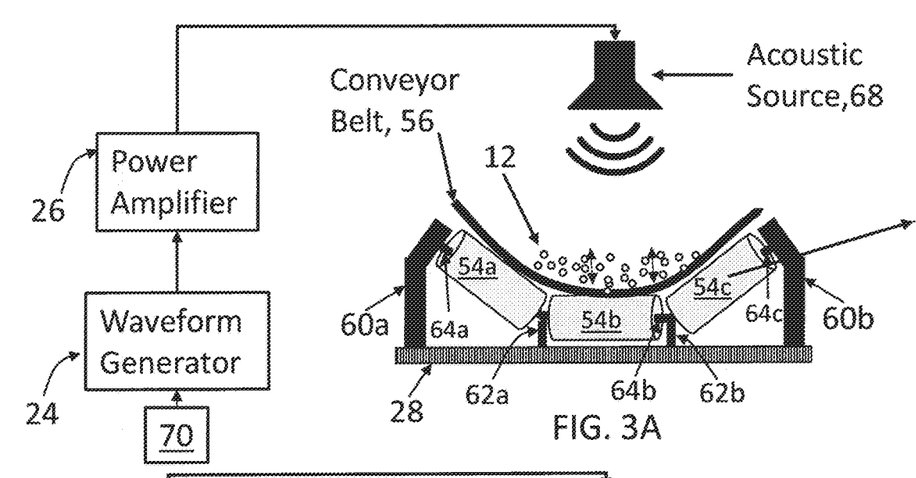
Figure 4:
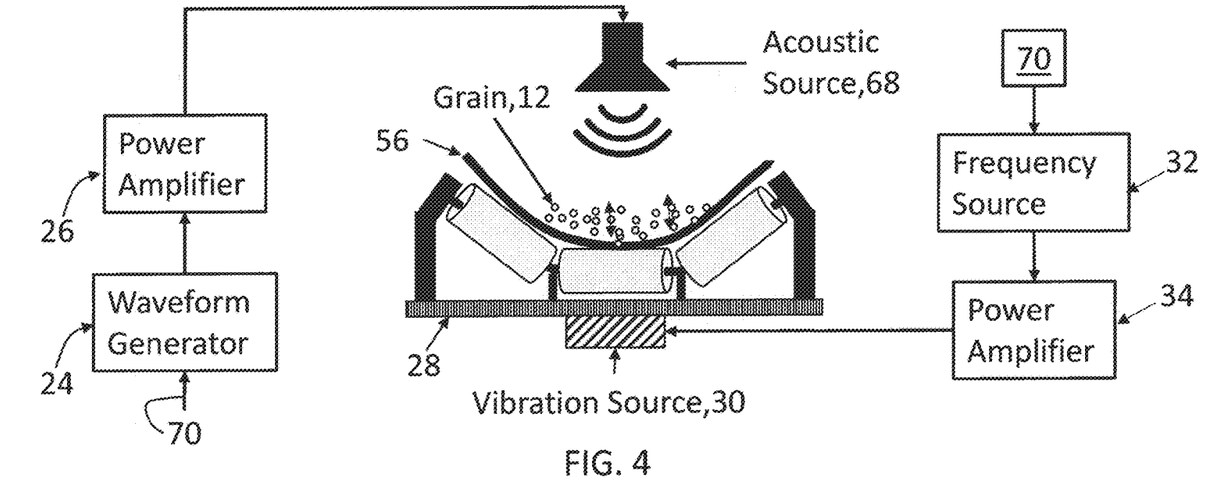
FIG. 4 is a schematic representation of a cross-section of another embodiment for providing external vibration to the conveyer belt using an acoustic transducer, the cylindrical rollers not providing vibration to the belt.

A typical conveyor system comprises a trough-shaped belt made from various types of rubber and polymers, which is moved on rollers by motorized driving wheels or pulleys, not shown in FIG. 3A or 4, generally in a loop. FIG. 3A is schematic representation of a cross section of an embodiment of conveyor system, 52, where idler rollers, 54a-54c, are disposed underneath belt, 56, in such a manner that belt 56 maintains an open concave shape while riding on multiple sets of rollers 54a-54c, suitable for containing grains 12, as grain 12 is carried by belt 56 from one location to another. Base, 28, supports a series of vertical roller supports, 60a, 60b, and 62a, 62b, supports 60a and 62a holding axle 64a upon which idler roller 54a rotates, supports 62a and 62b holding axle 64b upon which idler roller 54b rotates, and supports 62b and 60b holding axle 64c upon which idler roller 54c, rotates.

Figure 3B:
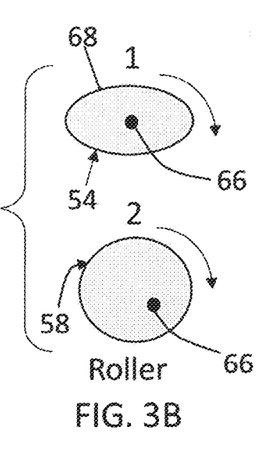
FIG. 3B is a schematic representation of cross-sections of two types of eccentric rollers for generating a fluidized bed of the grains, or any other kind of feed materials, by causing the belt vibrate and the grains to float over the bed; a high power and higher frequency acoustic source being disposed over the belt for forcing the floating grains to collide with one another.

To generate a fluidized bed of the grains, or any other kind of feed materials, belt 56 is vibrated. FIG. 3B is a schematic representation of cross sections of two types of eccentric rollers 54a-54c, where the top of the roller surface oscillates as it turns and, in turn, achieves suitable vibration in belt 56. Rollers 54 have an elliptical shape with centrally located cylindrical holes, 66, adapted for receiving one of the axles 64a-64c, whereby surface, 68, moves periodically between two heights. Cylindrical roller, 58, shown having off-centered cylindrical hole 66 adapted for receiving one of the axles, serves a similar function. Thus, when belt 56 passes over any of these rollers, it is caused to vibrate, thereby rendering grains 12 airborne a small distance above belt 56.

High-power and higher frequency (tens of kHz, for example, 20 kHz) acoustic source, 68, is disposed over belt 56, and is driven by a waveform generator, 24, and power amplifier, 26. Waveform generator 24 determines the frequency for high-frequency source, and also its waveform characteristics, and is controlled by a microcontroller, 70. The high-frequency acoustic waves force the floating grains to collide with each other. There may be a multiplicity of such sources placed along belt 56, and disposed at various angles, such that each volume of grain 12 is treated multiple times to ensure that the pathogen reduction is effective.

FIG. 4 is a schematic representation of a cross section of another embodiment for providing external vibration to belt 56. Transducer, 30, driven by acoustic frequency source 32 through amplifier 34, and controlled by microprocessor 70 is attached to the fixture or surface 28 that supports rollers 54a-54c. In this embodiment, rollers 54a-54c are cylindrical and have axle holes 66 along their cylindrical axes. Although, the acoustic transducer is shown as being attached to surface 28, it is not restricted to this location, and may be attached to vertical roller supports, 60a, 60b, and 62a, 62b as well. Acoustic sources having high power output are commercially available and are used in the food and beverage industries. Low-frequency vibration sources are also commercially available.

C. Destruction of Airborne Pathogens:

In normal room air (e.g., Class ISO 9), there are large number of particles of various kinds including, dust, pollen, bacteria, etc. The largest number of particles are >0.5 μm in size, as seen in the TABLE. If pathogens, such as bacteria or viruses, are present in the air, these attach to the other particles due to electrostatic charge, hydrodynamic induced attraction, van der Waal's forces, and several other forces, and random collisions. When the air is vibrated with low-frequency sound, for example, ~20 kHz, the amplitude of vibration is large, and the particles can efficiently collide with one another. Therefore, to destroy (inactivate) these pathogens, mechanical impact due to increased collisions among the pathogen-carrying particles plays an important role. Often, viruses, such as Covid-19 (0.125 μm in length; 0.085 μm in diameter; with spikes 0.020 μm long), and other viruses, are mechanically fragile and the outer membrane of such viruses can easily rupture thereby inactivating the virus.

TABLE

| | maximum particles/m³ | | | | | | FED STD 209E |
|---|---|---|---|---|---|---|---|
| Class | >=0.1 μm | >=0.2 μm | >=0.3 μm | >=0.5 μm | >=1 μm | >=5 μm | equivalent |
| ISO 1 | 10 | 2 | | | | | |
| ISO 2 | 100 | 24 | 10 | 4 | | | |
| ISO 3 | 1,000 | 237 | 102 | 36 | 8 | | Class 1 |
| ISO 4 | 10,000 | 2,370 | 1,020 | 362 | 83 | | Class 10 |
| ISO 5 | 100,000 | 23,700 | 10,200 | 3,620 | 823 | 29 | Class 100 |
| ISO 6 | 1,000,000 | 237,000 | 102,000 | 36,200 | 8,320 | 293 | Class 1,000 |
| ISO 7 | | | | 362,000 | 83,200 | 2,930 | Class 10,000 |
| ISO 8 | | | | 3,620,000 | 832,000 | 29,300 | Class 100,000 |
| ISO 9 | | | | 36,200,000 | 8,320,000 | 293,000 | Room Air |

The microorganism destruction embodiments presented above can be modified and extended to destroy airborne pathogens as well. For airborne pathogens, the step of rendering these objects equivalent to a fluidized bed in air, as for grains, is unnecessary, as these are already free-floating. On the other hand, the small particle size and the virus size require a preconditioning process where the small particles are caused to aggregate into small clusters, thereby appearing as larger particles, because small particles are entrained in air and, therefore, move with air flow.

This embodiment of the present invention applies the well-known acoustic radiation force (ARF) to first move airborne particles to standing wave nodal planes in a resonator chamber, whereby small clusters are formed. The force on a particle due to an acoustic wave, $F_a$, can be expressed as:

$$F_a = \left(\frac{\pi P_0^2 V_p \beta_f}{2\lambda}\right) \Phi \sin(2\kappa x), \quad (1)$$

where $P_o$ is the pressure amplitude, k is the wave number, λ is the wavelength, t is time, x is the local position within a transducer and a reflector, $V_p$ is the particle volume, $\beta_f$ is the fluid compressibility, and $\Phi$ is a material constant, respectively. See, e.g., K. Yosioka and Y. Kawasima, "Acoustic Radiation Pressure on a Compressible Sphere", Acustica, Vol. 5, pp. 167-173, 1955.

When the constant t is positive, the force will pull the particle toward the node, and when $\Phi$ has the opposite sign, the force will move the particle toward the anti-node. The material constant $\Phi$ is obtained by the following expression:

$$\Phi = \left(\frac{5\rho_p - 2\rho_f}{2\rho_p - 2\rho_f}\right) - \left(\frac{\beta_p}{\beta_f}\right), \qquad (2)$$

where $l_f$ and $\beta p$ are material compressibilities for the fluid medium (air) and particle, respectively. See e.g., L. A. Cruz, "Acoustic Force on a Liquid Droplet in an Acoustic Stationary Wave", J. of the Acoustical Society of America, Vol. 50, pp. 157-163, 1971.

As can be seen from Eq. (1), the acoustic force is proportional to the volume of the particle and, thus larger particles experience larger forces. The principal driver for the particle acoustic agglomeration is the nature of the acoustic signal, namely, the acoustic frequency, the acoustic intensity, and the residence time. In general, higher frequencies in the ultrasonic range perform better for particle agglomeration for sub-micron particles, whereas lower frequencies are effective for particles in the micron range, since small particles are entrained in air at low-frequencies and move with the air. These particles do not collide or follow the vibration of the acoustic wave. Although it appears obvious to use high frequencies for airborne pathogen destruction, there are two issues to consider. First, high frequencies, >200 kHz, attenuate strongly in air and, consequently, shorter distances and smaller geometries must be used for the apparatus for setting up standing waves resulting in particle agglomeration. For example, acoustic absorption in air at 25° C., 50% humidity, and at 10 kHz is 0.131 dB/m, as compared to 17.4 dB/m at 300 kHz. In addition, the residence times become too long for a practical device, one that has a reasonable quantity of air flow throughput. Second, the acoustic force is small and collisions among small particles are not very effective. Large particles become stationary at these high frequencies, and do not move from their equilibrium positions. Therefore, there are few collisions among the large particles.

Figure 5:
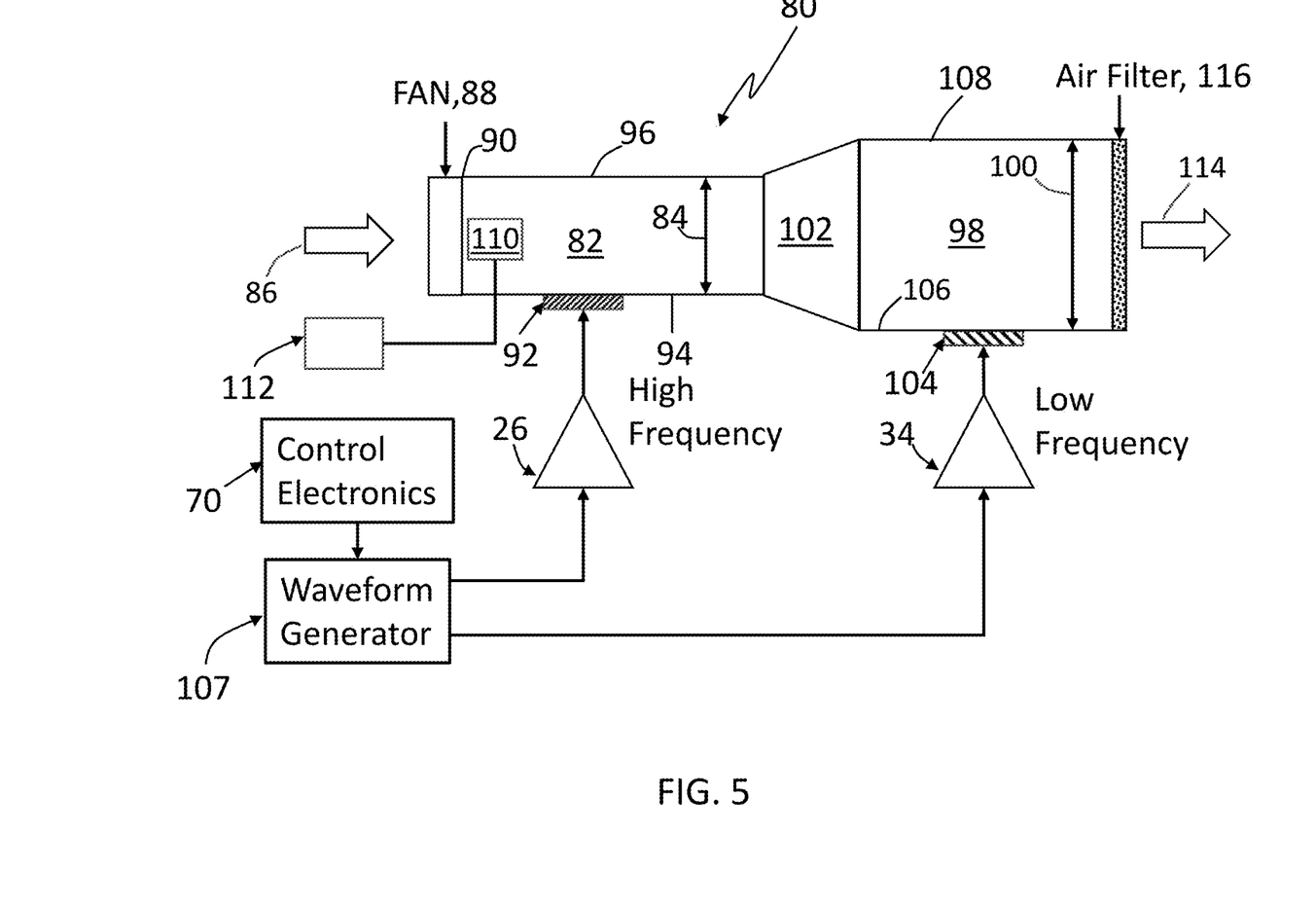
FIG. 5 is a schematic representation of a side view of an embodiment of an apparatus for destruction of airborne pathogens, wherein small particles in the air having viruses attached thereto, are caused to agglomerate using high frequencies (in the range between about 60 kHz and about 100 kHz) in a rectangular first acoustic chamber having small depth, while a second rectangular acoustic chamber, having larger depth, than the first rectangular acoustic chamber is vibrated at low frequencies (in the range between about 20 Hz and about 200 Hz) for causing the agglomerated particles to collide.

An effective approach is a two-step process. Turning to FIG. 5, a schematic representation of a side view of apparatus, 80, for noninvasive destruction of airborne pathogens is illustrated. Preconditioning of the air is accomplished at high frequencies (in the range between about 100 kHz and about 500 kHz) in rectangular first acoustic chamber (20 cm×15 cm), 82, having depth (2 cm), 84. Air, 86, is driven into chamber 82 using fan, 88, at entrance, 90, thereto. An acoustic wave is generated by a piezoelectric transducer, 92, in vibrational communication with one side, 94, of chamber 82, driven by waveform generator 24 through amplifier 26, and controlled by electronics 70, while opposing side, 96, functions as a reflector such that a standing wave pattern of parallel nodal planes is generated inside chamber 82. The separation between the nodal planes is related to the wavelength of the applied sound in air (e.g., 1 mm wavelength at 340 kHz). The chamber dimension is based on the size of the driving transducer. A larger rectangular-shaped transducer or multiple smaller transducers driven with the same driving signal can accommodate a larger chamber. The purpose of this high-frequency preconditioning is to produce clusters of particles carrying pathogens attached to those particles, which then behave as larger particles. During the agglomeration process when the particles move closer together, there is a secondary acoustic force that assists in the collision process and in binding the particles together. First acoustic chamber 82 is not very effective for pathogen destruction or inactivation, although a certain amount of inactivation is possible depending on the pathogen.

Second rectangular acoustic chamber, 98, is larger in depth (by as much as a factor of 2.5, and depends on the low-frequency used and on the applied acoustic power), 100, than first rectangular acoustic chamber 82, but has almost the same volume as chamber 82, for maintaining the air throughput reasonably constant. Transition member, 102, connects chambers 82 and 98, for reduces air turbulence. Low-frequency transducer (in the range between about 5 kHz and about 50 kHz), 104, in vibrational communication with side, 106, of chamber 98 is driven by waveform generator, 107, through amplifier 34, and controlled by electronics 70, generates an acoustic wave in chamber 98. Opposing side, 108, functions as a reflector such that a standing wave pattern of parallel nodal planes is generated inside chamber 98. The nodal planes are much more widely separated (e.g., 3.4 cm at 10 kHz) than in chamber 82. The configuration of chamber 98 is chosen based on the desired flow rate of the apparatus.

Programmable electronic control device 70, such as an Arduino or Raspberry Pi electronics board, may be used to control dual output waveform generator 107. The amplitude and frequency of each channel of dual-output generator 107 can be programmed; therefore, both the high-frequency and the low-frequency output signals for apparatus 80 are provided by waveform generator 107 through power amplifiers 26 and 34, respectively, one for each channel to drive transducers 92 and 104, respectively.

Applied vibrational frequencies for the two chambers are adjusted such that the small clusters more efficiently agglomerate to form larger particles as a result of the larger acoustic forces in chamber 82. Chamber 98 is the location where large numbers of interparticle collisions take place, since the particles tend to accumulate at the few nodal planes after moving from their original locations. In chamber 98, the particles vibrate with the applied sound wave, and collide with their nearest neighbors. For example, at 10 kHz, the particles will collide almost 10,000 times per second. To improve the pathogen inactivation, chamber 98 can be lengthened (pathogen treatment length), if needed, since the chamber length determines the residence, which depends on the flow rate.

Chambers 82 and 98, and transition member 102 may comprise metal, such as steel, brass, or copper, as examples. Transducers 92 and 104 may comprise piezoelectric transducers, but any transducer generates effective vibrations in the required frequency ranges can be used. The transducers are typically epoxied to the outer surfaces of the chamber and vibrate a large portion of the chamber wall beyond the transducer surface area. Although, transducers 92 and 104 are illustrated as single transducers, multiple transducers can be used to cover large surface areas, as needed.

It is well known that heat destroys most air-borne pathogens, including various types of influenza viruses. The temperature of air 86 can be increased by attaching electrical heaters, 110, controlled by temperature controller, 112, outside of either or both chambers 82 and 98. Air, 114, exiting pathogen treatment apparatus 80 may be filtered by filter, 116, effective for removing particles greater than 5 μm; a HEPA-type filter is not utilized since that type of filtration significantly reduces the flow rate.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for destruction of microorganisms residing on the surfaces of grains and dried food, comprising:
    a conveyor belt having a trough-shaped carrying side onto which are deposited grains or dried food, and a lower side supported by at least one set of 3-roller trough idlers, each idler having an axle;
    a first source of vibration for applying a first periodic vibrational excitation having a first amplitude to the at least one set of 3-roller trough idlers, effective for creating a fluidized bed of the grains or dried food above the surface of said conveyor belt; and
    a second source of periodic vibrational excitation having a second amplitude spaced apart from, and above said conveyor belt for vibrating the fluidized grains or dried food, effective for causing the grains or dried food to undergo increased collisions therebetween;
    whereby the microorganisms are destroyed by collisions of the grain or dried food.

2. The apparatus of claim 1, wherein said first source of vibration comprises a vibrational transducer adapted for vibrating the at least one set of 3-roller trough idlers, and powered by a frequency source driving a power amplifier.

3. The apparatus of claim 2, wherein the first periodic vibrational excitation comprises a fixed frequency vibrational excitation.

4. The apparatus of claim 2, wherein the first periodic vibrational excitation comprises a swept frequency vibrational excitation.

5. The apparatus of claim 4, wherein the first periodic vibrational excitation comprises a square-wave.

6. The apparatus of claim 5, wherein the square-wave is swept in frequency between 10 Hz and 100 Hz.

7. The apparatus of claim 1, wherein said first source of vibration comprises eccentric rollers or off-centered axles for each roller in said at least one set of 3-roller trough idlers.

8. The apparatus of claim 1, wherein the second periodic vibrational excitation comprises a fixed frequency vibrational excitation.

9. The apparatus of claim 1, wherein the second periodic vibrational excitation comprises a swept frequency vibrational excitation.

10. The apparatus of claim 9, wherein the second periodic vibrational excitation comprises a square-wave.

11. The apparatus of claim 10, wherein the square-wave is swept in frequency between 5 kHz and 100 KHz.

12. The apparatus of claim 1, further comprising a temperature measuring device for measuring the air temperature above the surface of said conveyor belt.

* * * * *

UNITED STATES PATENT AND TRADEMARK OFFICE
CERTIFICATE OF CORRECTION

PATENT NO. : 12,114,674 B2
APPLICATION NO. : 17/349525
DATED : October 15, 2024
INVENTOR(S) : Dipen N. Sinha

Page 1 of 1

It is certified that error appears in the above-identified patent and that said Letters Patent is hereby corrected as shown below:

On the Title Page

Item (73), should read as follows:
AWE Technologies, LLC, Bay Shore, New York (US)

Signed and Sealed this
Twenty-sixth Day of November, 2024

Katherine Kelly Vidal
*Director of the United States Patent and Trademark Office*